(12) United States Patent
Kwon et al.

(10) Patent No.: US 9,175,288 B2
(45) Date of Patent: Nov. 3, 2015

(54) COMPOSITION COMPRISING MIRNA FOR ENHANCING RADIATION SENSITIVITY

(71) Applicant: Korea Institute of Radiological & Medical Sciences, Seoul (KR)

(72) Inventors: Hee Chung Kwon, Namyangju-si (KR); Eun Sook Kim, Seoul (KR); Jie Young Song, Goyang-si (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 0 days.

(21) Appl. No.: 14/265,143

(22) Filed: Apr. 29, 2014

(65) Prior Publication Data

US 2015/0141486 A1  May 21, 2015

(30) Foreign Application Priority Data

Nov. 18, 2013  (KR) ........................ 10-2013-0140091

(51) Int. Cl.
 *C12N 15/11* (2006.01)
 *C12N 15/113* (2010.01)
(52) U.S. Cl.
 CPC ........ *C12N 15/113* (2013.01); *C12N 2310/141* (2013.01); *C12N 2330/51* (2013.01)

(58) Field of Classification Search
 CPC ...................... C12N 2310/14; C12N 2310/141
 See application file for complete search history.

(56) References Cited

U.S. PATENT DOCUMENTS

2009/0176723 A1* 7/2009 Brown et al. ................... 514/44

OTHER PUBLICATIONS

Gregory et al., "The Microprocessor complex mediates the genesis of microRNAs," *Nature*, vol. 432, pp. 235-240, Nov. 11, 2004.
Kim et al., "MicroRNA-499b-5p functions as a radiosensitizer by negatively regulating of ATM," *2013 KSRB Spring Conference, Korean Society of Radiation Bioscience* (Poster and Abstract), 4 pp., Jun. 20, 2013.
Lee et al., "The nuclear RNase III Drosha initiates microRNA processing," *Nature*, vol. 425, pp. 415-419, Sep. 25, 2003.
Lim et al., "Acriflavine enhances radiosensitivity of colon cancer cells through endoplasmic reticulum stress-mediated apoptosis," *The International Journal of Biochemistry & Cell Biology*, 44, pp. 1214-1222, May 4, 2012.
Pillai et al., "Repression of protein synthesis by miRNAs: how many mechanisms?," *TRENDS in Cell Biology*, vol. 17, No. 3, pp. 118-126, Jan. 2, 2007.

* cited by examiner

*Primary Examiner* — Brian Whiteman
(74) *Attorney, Agent, or Firm* — Klarquist Sparkman, LLP

(57) ABSTRACT

Provided are a method of enhancing radiation sensitivity by using miR-499b-5p and a method of treating a radiation resistant cancer including administering miR-499b-5p.

4 Claims, 6 Drawing Sheets miR-499b-5p    3'- UUUGUAGUGACGUUCAGAAUU - 5'
ATM-3'UTR (wt)   5' - AAAAUGUUUUGAUGGUCUUAA - 3'
ATM-3'UTR(Δ6)    5' - AAAAUGUUUUGAUG ****** A - 3'

* Putative miR-499b-5p binding domain
: 175-181 of human ATM 3' UTR

SEQUENCE LISTING

```
<160> NUMBER OF SEQ ID NOS: 9

<210> SEQ ID NO 1
<211> LENGTH: 21
<212> TYPE: RNA
<213> ORGANISM: Homo sapiens

<400> SEQUENCE: 1
acagacuugc ugugauguuc a                                              21

<210> SEQ ID NO 2
<211> LENGTH: 20
<212> TYPE: DNA
<213> ORGANISM: Artificial Sequence
<220> FEATURE:
<223> OTHER INFORMATION: p53 forward primer

<400> SEQUENCE: 2
ctgccttccg ggtcactgcc                                                20

<210> SEQ ID NO 3
<211> LENGTH: 20
<212> TYPE: DNA
<213> ORGANISM: Artificial Sequence
<220> FEATURE:
<223> OTHER INFORMATION: p53 reverse primer

<400> SEQUENCE: 3
ttgggacggc aaggggggaca                                               20

<210> SEQ ID NO 4
<211> LENGTH: 19
<212> TYPE: DNA
<213> ORGANISM: Artificial Sequence
<220> FEATURE:
<223> OTHER INFORMATION: GAPDH forward primer

<400> SEQUENCE: 4
ccgtctagaa aaacctgcc                                                 19

<210> SEQ ID NO 5
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 5
gccaaattcg ttgtcatacc                                                20
```

```
<210> SEQ ID NO 6
<211> LENGTH: 23
<212> TYPE: DNA
<213> ORGANISM: Artificial Sequence
<220> FEATURE:
<223> OTHER INFORMATION: ATM forward primer

<400> SEQUENCE: 6
tgctgacaat catcaccaag ttc                                              23

<210> SEQ ID NO 7
<211> LENGTH: 20
<212> TYPE: DNA
<213> ORGANISM: Artificial Sequence
<220> FEATURE:
<223> OTHER INFORMATION: ATM reverse primer

<400> SEQUENCE: 7
tctcccttcc tgtcctggaa                                                  20

<210> SEQ ID NO 8
<211> LENGTH: 21
<212> TYPE: RNA
<213> ORGANISM: Homo sapiens
<220> FEATURE:
<223> OTHER INFORMATION: miR-499b-5p

<400> SEQUENCE: 8 uuuguagugacguucagaauu                                                  21

<210> SEQ ID NO 9
<211> LENGTH: 21
<212> TYPE: RNA
<213> ORGANISM: Homo sapiens
<220> FEATURE:
<223> OTHER INFORMATION: ATM 3'UTR

<400> SEQUENCE: 9 aaaauguuuugauggucuuaa                                                  21
```

COMPOSITION COMPRISING MIRNA FOR ENHANCING RADIATION SENSITIVITY

CROSS REFERENCE TO RELATED APPLICATION

This application claims the benefit of Korean Patent Application No. 10-2013-0140091, filed on Nov. 18, 2013, with the Korean Intellectual Property Office, the disclosure of which is incorporated herein in its entirety by reference.

FIELD

One or more embodiments of the present invention relate to a method of enhancing radiation sensitivity by using miR-499-5p and a method of treating a radiation resistant cancer including administering miR-499b-5p, and more particularly, to miR-499b-5p for enhancing radiation sensitivity of a cancer cell by downregulating expression of ATM (Ataxia telangiectasia mutated) gene, and its use as a therapeutic agent for a combination therapy with radiation therapy.

BACKGROUND

Breast cancer and lung cancer, both being solid tumors, have been considered as major causes of cancer deaths regardless of multimodality therapies therefor. Radiation therapy is a general therapeutic method performed on a solid tumor patient. Solid tumor patients account for about 40% to 60% of cancer patients receiving radiation therapy. However, solid tumors have been known to show radioresistance which reduces the killing of cancer cells by radiation therapy. Accordingly, for effective cancer treatment, there is a need for the development of a radiosensitizer that can enhance cancer cell killing by irradiation.

An miRNA (microRNA) is a very small single stranded ribonucleic acid (RNA) consisting of about 21 to 23 nucleotides, found in cells. About a few hundred miRNAs are known to be present in humans, and to be involved in biological phenomena such as development, growth, aging and death via regulation of gene expression. Due to the distinctive expression patterns of miRNA in normal tissues and cancer tissues, the utility of miRNA as a predictive biomarker has been noted. In particular, miR-21 has been known to mediate the pathophysiological mechanism of tumor development by playing a critical role in proliferation, invasion and metastasis of a tumor by targeting a tumor suppressor gene.

Ionizing radiation (IR) eventually leads to deoxribonucleic acid (DNA) damage in cells, thereby causing cell death. A double strand break (DSB) due to IR induces DNA damage response (DDR) signal transduction, which is known to determine cell cycle arrest for DNA repair or apoptosis due to excessive DNA damage. miRNAs which target major genes involved in the DDR signal transduction have been already reported, and thus miRNAs' new roles in the radiation induced DDR signal transduction are of great concern. With new human miRNAs being continuously discovered, there has been an increasing need for the development of a therapeutic agent that is capable of enhancing radiation sensitivity while minimizing any adverse effect, thereby providing effective therapy to be combined with radiation therapy.

Accordingly, the inventors of the present invention have focused their research on miRNA which can be used as a radiosensitizer in combination with radiation therapy by acting on major genes involved in the DDR signal transduction, and succeeded in developing miRNA capable of increasing radiation sensitivity of radioresistant cancer cells.

These and/or other aspects will become apparent and more readily appreciated from the following description of the embodiments, taken in conjunction with the accompanying drawings.

SUMMARY

Figure 1:
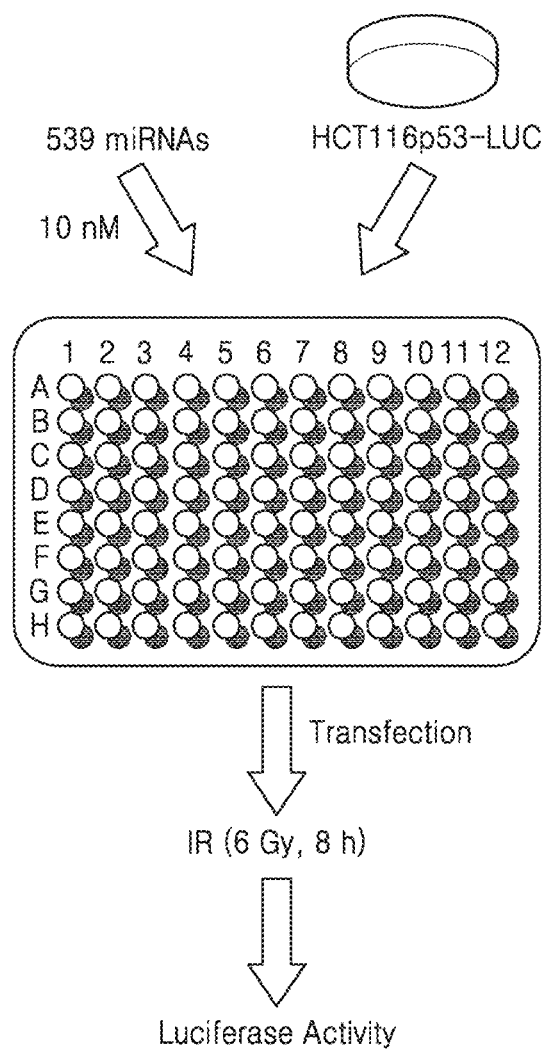
FIG. 1 is a schematic diagram illustrating a screening of an miRNA library by using HCT116p53-LUC, a human colon cancer cell line, for selecting an miRNA capable of enhancing radiation sensitivity.

Provided herein are methods of enhancing radiation sensitivity by using miR-499b-5p. Also provided are methods of treating a radiation resistant cancer including administering miR-499b-5p.

DETAILED DESCRIPTION

One or more embodiments of the present invention provide miR-499b-5p for enhancing radiation sensitivity.

One or more embodiments of the present invention provide a method of treating a radiation resistant cancer, the method comprising administering to a subject in need thereof miR-499b-5p in an amount effective to enhance radiation sensitivity of cancer cells and applying radiotherapy.

According to an aspect of the present invention, there is provided miR-499b-5p of SEQ. ID. NO. 1 for enhancing radiation sensitivity.

As used herein, the term, "radiation sensitivity enhancement" refers to increasing the effect of radiation therapy by enhancing the radiation sensitivity of radioresistant cells. As used herein, the term, "radiation sensitivity" refers to the susceptibility of a cell or subject to physical or chemical changes induced by radiation. An agent or composition for enhancing radiation sensitivity is used as a treatment, i.e., radiosensitizer for use in combination with radiation therapy. When the radiation sensitivity of a cancer cell is enhanced, cytotoxicity and anti-proliferative effect of radiotherapy on cancer cells also increase.

miRNAs are mostly present in introns of chromosomes in a cell. A miRNA is transcribed into a primary miRNA by RNA polymerase II, and then cleaved by RNase III such as Drosha and Pasha, to produce a pre-miRNA (precursor miRNA) in a nucleus. Then, the precursor miRNA is transported from the nucleus into cytoplasm by Exportin-5, and is cleaved by Dicer, a RNase III into short double stranded miRNA fragments about 22 bp length in the cytoplasm. Then, the miRNA is separated into a single strand by binding to an RNA interference silencing complex (RISC), and the single stranded miRNA binds to a nucleotide sequence of 3'-untranslated region (UTR) of a target mRNA via complementary base pairing, resulting in gene silencing via translational regression or target mRNA degradation (Nature, 425(6956): 415-9, 2003; Nature, 432(7014): 235-40, 2004; and Trends Cell Biol., 17:118-126, 2007).

miR-499b-5p was selected as miRNA that efficiently reduced the radiation induced p53 activation in a screening of a library of human miRNAs using a human colon cancer cell line HCT116p53-LUC which stably expresses a DNA including 12 repeats (12×) of a p53-specific binding domain in a promoter region of p53 gene, a major gene in DDR signal transduction, and a luciferase as a reporter gene.

In the human colon cancer cell line HCT116 p53(wild-type), it was found that an overexpression of miR-499b-5p reduces the expression of p53 gene in the cancer cell, and enhances radiation sensitivity of the cancer cell after 6 Gy irradiation, compared to the control miRNA. Furthermore, it was confirmed via a TargetScan analysis program (accessible on the world wide web at targetscan.org) that "CAGAAU" (nucleotides 15-20 of SEQ ID NO: 8), a hexanucleotide in miR-499b-5p, is a region that binds to 3'UTR of ATM ("GU-CUUAA", positions 175 to 181 or 15-21 of SEQ ID NO:9) (Human ATM NM_000051 3' UTR length: 3591), a major molecule involved in radiation induced DNA damage and repair mechanism.

Accordingly, it was found that the miR-499b-5p can be advantageously used as an active radiosensitizer in radiotherapy for cancer by enhancing radiation sensitivity of radioresistant cancer cells.

miR-499b-5p binds to 3'-UTR of ATM, thereby significantly reducing the expression of ATM gene and thus enhancing sensitivity to radiation.

In an embodiment of the present invention, the miR-499b-5p may have the sequence set forth SEQ. ID. NO. 1 (Accession No: MIMAT0019897, sequence: ACAGACUUGCU-GUGAUGUUCA) but is not limited thereto, and any sequence having 80% or more of homology to the sequence may be used. The miR-499b-5p may be about 18 to 25 nucleotides or more in length, and it may include any variant thereof, which is modified via deletion, substitution, or insertion, while still being capable of performing a function equivalent to that of miR-499b-5p.

In an embodiment of the present invention, the miR-499b-5p may be used to enhance radiation sensitivity of cancer cells.

The miRNA-499-5p of the present invention enhances radiation sensitivity by decreasing radioresistance of radioresistant cancer cells by binding to ATM in cells to inhibit the expression of p53 gene. The miRNA-499-5p may be applicable to any type of cells to which radiation therapy may be applied, and in particular, to cancer cells for enhancing their radiation sensitivity.

It was found that the overexpression of miRNA-499-5p enhances radiation sensitivity of cancer cells having strong radioresistance, such as colon cancer, breast cancer, and lung cancer cells.

In an embodiment of the present invention, the cancer may be selected from the group consisting of breast cancer, colon cancer, lung cancer, head and neck cancer, prostate cancer, uterine cancer, brain tumor and lymphoma, but is not limited thereto.

In an embodiment of the present invention, the miR-499b-5p may be provided in an expression vector for intracellular delivery or may be provided in a cell capable of expressing it. The expression vector may be a plasmid DNA or a recombinant virus vector.

The miRNA of the present invention may be introduced into a cell via various transformation techniques, and to this end, the miRNA may be included in a carrier for efficient introduction into a cell. The carrier may be a vector, a viral vector or a non-viral vector. The viral vector may include, for example, lentivirus, retrovirus, adenovirus, herpes virus and avipox virus vectors, and in particular, lentivirus vector, but is not limited thereto. Lentivirus is a retrovirus species which can infect both divided cells and undivided cells due to the nucleophilicity of its pre-integration complex (virus shell) which enables an active transport through a nucleopore or a nuclear membrane.

Upon introduction into cancer cells, the miRNA of the present invention may enhance radiation sensitivity of cancer cells. As used herein, the term "introduction" refers to incorporating foreign DNA into a cell via transfection or transduction.

Transfection may be performed via various methods known in the art such as a calcium phosphate-DNA coprecipitation method, DEAE-dextran-mediated transfection, polybrene-mediated transfection, electroporation, microinjection, liposome fusion, lipopectamine and protoplast fusion. Transduction refers to transfer of a gene into a cell via infection using a virus or a bacteriophage vector.

According to an aspect of the present invention, there is provided a composition including miR-499b-5p of SEQ. ID. NO. 1 for enhancing radiation sensitivity.

The composition including the miRNA-499-5p for enhancing radiation sensitivity may further include a pharmaceutically acceptable carrier, and the composition may be formulated along with the carrier.

As used herein, the term, "a pharmaceutically acceptable carrier" refers to a carrier or a diluent which does not inhibit a physiological activity or property of an active compound to be administered and does not irritate the subject. The pharmaceutically acceptable carrier in a composition to be formulated into a form of solution may include at least one of saline solution, sterilized water, Ringer's solution, buffered saline, albumin injection solution, dextrose solution, maltodextrose solution, glycerol, ethanol, and combinations thereof, which are suitable for sterilization and biocompatible. Other conventional additives such as an antioxidant, a buffer solution, and a bacteriostat may be added, if desired. In addition, the composition may further include a diluent, a dispersant, a surfactant, a binder, and a lubricant and be formulated into a form for injection such as an aqueous solution, a suspension, and an emulsion, a pill, a capsule, granules, or a tablet.

The composition including the miRNA-499-5p and the pharmaceutically acceptable carrier of the present invention may be administered in any form of formulation, for example, either an oral or parenteral formulation, and may be formulated into a unit dosage form for ease of administration and uniformity of dosage. The formulations of the composition of the present invention may include those suitable for oral, rectal, nasal, topical, subcutaneous, vaginal or parenteral administration, or those suitable for inhalation or insufflation.

The composition for enhancing radiation sensitivity of the present disclosure may be prepared as a form for injection to be injected to a tumor region to be treated by radiotherapy, as a form of a gel composition or a formulation for a transdermal delivery to directly apply or attach it to the tumor region, or as a form of a suppository to be inserted, or as a form of an aerosol preparation to be inhaled through a respiratory tract. For injection, the composition may be prepared as a solution or a suspension by mixing it with a stabilizer or a buffer in water, which may be formulated into a unit dosage form such as an ampoule or a vial. For a suppository, the composition may be prepared as a conventional suppository including a suppository base or a composition for rectal injection such as a clyster. For a spray such as an aerosol, a propellant may be added along with an additive so that water-borne concentrate or wet powder may be well dispersed.

In another aspect of the present invention, there is provided a method of treating a radioresistant cancer including administering miR-499b-5p and applying radiation therapy.

In an embodiment of the present invention, miR-499b-5p is administered in a composition for enhancing radiation sensitivity including miRNA-499-5p.

In an embodiment of the present invention, the miR-499b-5p may have the sequence set forth in SEQ. ID. NO. 1 (Accession No: MIMAT0019897, sequence: ACAGACUUGCU-GUGAUGUUCA) but is not limited thereto, and any sequence having 80% or more of homology to the sequence may be used. The miR-499b-5p may be about 18 to 25 nucleotides or more in length, and it may include any variant thereof, which is modified via deletion, substitution, or insertion, while being capable of performing a function equivalent to that of miR-499b-5p.

The composition for enhancing radiation sensitivity including the miRNA-499-5p of the present invention may further include a pharmaceutically acceptable carrier, and may be formulated along with the carrier.

As used herein, the term, "administration" refers to delivery of the composition of the present invention into a subject by an appropriate method, and may include delivery via a viral or non-viral vehicle of the miRNA-499-5p. Once the composition of the present invention is introduced into a cancer cell, it downregulates the expression of ATM thus enhancing the radiation sensitivity of the cancer cell.

The composition of the present invention may be administered through various routes to deliver it to a target site, including an oral or parenteral route, more specifically, through a conventional route of an oral, rectal, topical, intravenous, intraperitoneal, intramuscular, intra-aortic, percutaneous, intranasal, inhalation, intraocular, or intracutaneous administration. The composition of the present invention may be topically administered to the target site.

The method of treating a radioresistant cancer of the present invention includes administering a therapeutically effective amount of the composition for enhancing radiation sensitivity. The therapeutically effective amount refers to an amount which can effectively enhance the sensitivity of cancer cells to radiation. It will be obvious to a person of ordinary skill in the art that an appropriate daily dosage of the therapeutically effective amount of the composition may be readily determined by a physician within the appropriate scope of medical diagnosis. For a particular subject, the specific therapeutically effective amount of the composition may vary depending on relevant factors such as the type and degree of the response to be achieved, a specific composition used, age, body weight, general physical state, sex, and diet of the subject, time and route of administration, release rate of the composition, period of treatment, and the radiation dose. Accordingly, the therapeutically effective amount of the composition for enhancing radiation sensitivity in the present invention may be determined in consideration of the above factors. Additionally, the composition of the miR-499b-5p for enhancing radiation sensitivity may be administered along with a known anticancer agent to enhance the effect of the cancer treatment including radiation therapy.

Also, the method of treating a radioresistant cancer according to the present invention may be applied to a subject whose radiation sensitivity can be enhanced by decrease in p53 expression and ATM expression attributable to the administration of the miR-499b-5p. The subjects may include cows, pigs, sheep, horses, dogs, and cats in addition to humans and primates, but is not limited thereto.

In an embodiment of the present invention, the cancer may be selected from breast cancer, colon cancer, lung cancer, head and neck cancer, prostate cancer, uterine cancer, brain tumor, and lymphoma, but is not limited thereto.

The method of treating a radioresistant cancer of the present invention includes administering a composition of the present invention and applying irradiation for radiation therapy. As used herein, the term "irradiation" refers to ionizing radiation (IR), in particular, gamma radiation generated by a conventional linear accelerator or radionuclide. The term "radiation therapy" is used herein interchangeably with "radiotherapy". The radiation therapy administered to tumors by using a radionuclide may be performed externally or internally.

In an embodiment of the present invention, the composition including the miR-499b-5p may be administered before applying radiation therapy, in particular, about a month before, more particularly, a week or 10 days before. Additionally, when applying the radiation therapy, it may be desirable that the composition of the present invention be administered continually between the first irradiation and the final irradiation.

The amount of the miRNA-499-5p to be administered, the radiation dose, and the frequency of irradiation may be determined based on factors including the type and the location of the cancer to be treated, and the response of a subject to chemotherapy or radiation therapy.

Advantageous Effects of the Invention miR-499b-5p of the present invention enhances radiation sensitivity of radioresistant cancer cells by down regulating expression of ATM gene in the cancer cells. Accordingly, the miR-499b-5p of the present invention can be used as a potential therapeutic agent for use in combination with radiation therapy, thereby greatly enhancing the effect of radiation therapy.

MODE FOR INVENTION

Hereinafter, the present invention will be described more specifically with reference to the following examples. The following examples are only for illustrative purposes and are not intended to limit the scope of the invention.

Example 1

High Throughput Screening of miRNA Capable of Enhancing Radiation Sensitivity by Using Human Colon Cancer Cell Line HCT116p53-Luciferase 1-1. Cell Culture A human colon cancer cell line HCT116p53-luciferase, a HCT116p53 wild type, a breast cancer cell line MCF-7, and a lung cancer cell line H460 were respectively cultured at 37° C. in a humidified chamber supplied with 5% $CO_2$ in RPMI-1640 (LM011-01, Welgene Inc.) or DMEM (LM001-05, Welgene Inc.) with 10% fetal bovine serum (FBS), 100 U/mL of penicillin, and 100 μg/mL of streptomycin sulfate.

For ease of detection of an increase in p53 expression, HCT116p53-luciferase (HCT116p53-LUC) was produced by transfecting HCT116, a human colon cancer cell line (p53 wild type) with a luciferase reporter vector having twelve repeats of p53-specific binding domain present in a promoter of a p53 gene. Briefly, HCT116 cells were transfected with a p53-Luc reporter vector by using Lipofectamine 2000 (Invitrogen, USA) according to the manufacturer's instructions to obtain stably transfected cells, and then the stably transfected cells were selected by using a medium containing G418 (1 mg/mL) (see The International Journal of Biochemistry & Cell Biology 44(2012)1214-1222).

It has been known that p53 maintains a low level of expression under normal conditions and has a short life-span, but increases the level of expression when exposed to stresses such as irradiation or an anticancer agent, and is also involved in deoxyribonucleic acid (DNA) damage signal transduction. Confirming that HCT116p53-luciferase exhibits luciferase activity in proportion to the increase in the level of p53 expression, the HCT116p53-luciferase was used to select miRNA capable of enhancing radiation sensitivity.

1-2. Irradiation

For ionizing radiation (IR), gamma IR was irradiated by using a Gammacell 3000 Elan irradiator ([137Cs] γ-ray source; MDS Nordin, Canada).

1-3. Screening of miRNA Capable of Enhancing Radiation Sensitivity Via p53-Luciferase Activity In order to confirm the effect of the expression of miRNA on radiation sensitivity, miRNA was transfected into the human colon cancer cell line HCT116p53-luciferase by using G-fectin (Genolution, Korea), and the effect of irradiation on the expression of p53, i.e., the luciferase activity was measured.

The screening was performed using a library of 539 miRNAs (Genolution Pharmaceuticals Inc.) selected based on published references related to p53, cell proliferation and cell cycle.

First, 10 nM of respective miRNA and 1 μL of G-fectin were added to each well of a 96-well plate, and then OPTI-MEM (Invitrogen, U.S.A.) was added to a final volume of 10 μL, and incubated at room temperature. After 10 minutes, HCT116p53-luciferase was added into the 96-well plate at a concentration of $2 \times 10^4$ cells/90 μL/well for transfection. 24 hours after the transfection, luciferase activity of cells in the control group without irradiation and those in the treatment group with irradiation (6 Gy, 8 hours) was measured by using a Luciferase reporter assay kit (BioVison), respectively. FIG. 1 is a schematic diagram illustrating a screening of miRNA based on the measured activity of p53-luciferase.

Figure 2:
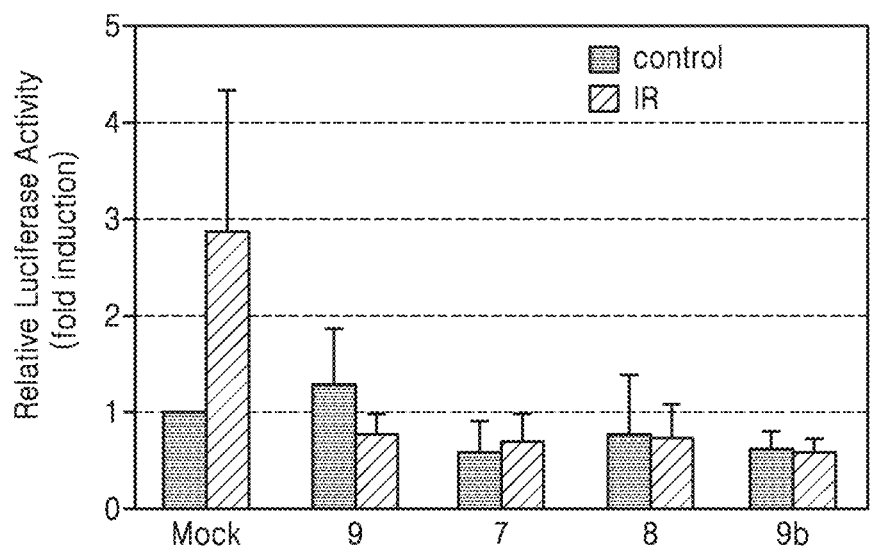
FIG. 2 is a graph illustrating the activity of p53-luciferase in HCT116p53-LUC cells which were transfected with miRNAs and then irradiated.

Using a library consisting of a total of 539 human miRNAs, the activity of the luciferase was measured in three replicates and 4 miRNAs were selected that lead led to decrease in luciferase activity upon irradiation, compared to that of the control group where the cells were not transfected with miRNAs. FIG. 2 shows the luciferase activity measured in the cells after irradiation. The Mock indicates the group processed in the same procedure as the miRNA transfected cells except that the cells were not transfected with miRNA. Compared to the Mock group, the groups, each group transfected with one of the selected miRNAs, i.e., 9, 7, 8, and 9b showed decrease in luciferase activity after irradiation. In FIG. 2, control refers to without irradiation and IR refers to with irradiation Example 2

Effect of Overexpression of Selected miRNAs on Level of p53 mRNA and Protein 2-1. Decrease in Expression of p53 Protein Due to Overexpression of Four Selected miRNAs In order to measure the change in the expression level of intracellular p53 protein regarding the four miRNAs selected in Example 1, each of the four miRNAs was transfected into a human colon cancer cell line HCT116 (p53 wild type) and the change in expression of p53 protein was observed via western blot analysis.

$4 \times 10^5$ of the HCT116 (p53 wild type) cells were prepared in each well of a 6-well plate one day prior to the transfection. 10 μL of Lipofectamine 2000 (Invitrogen) and 250 μL of OPTI-MEM were added to a tube, and 100 nM miRNA and OPTI-MEM were added to another tube to a final volume of 250 μL and incubated at room temperature, respectively. After incubation at room temperature for 5 minutes, the resulting contents of the two tubes were mixed together and incubated at room temperature for 20 minutes, and then added into the HCT116 (p53 wild type) cells which were prepared a day earlier. After 24 hours, the cells were separated and divided into two groups and irradiated (6 Gy) the following day. 8 hours after the irradiation (6 Gy), cell proteins were extracted by using a Proprep-protein extraction solution (Intron Biotechnology, PROPREP™ protein extraction buffer), and the proteins were quantified using a Bradford assay (Bio-Rad). The proteins were then separated via SDS-PAGE, transferred onto a nitrocellulose membrane. The nitrocellulose membrane was blocked with 5% skim milk solution in 0.05% TBST (mixture of Tris-Buffered Saline and Tween 20). Then, a primary antibody (anti-p53 (Santa Cruz Biotechnology), anti-ATM (Epitomics), anti-GAPDH (Cell Signaling), and anti-β-actin (Sigma)) was added thereto, and allowed to react at 4° C. overnight, and the membrane was washed with 0.05% TBST solution. Then, a secondary antibody (goat-anti-mouse Ig-HRP or goat-anti-rabbit-HRP, Santa Cruz Biotechnology) was added thereto, allowed to react at room temperature for 1 hour, and the membrane was washed with 0.05% TBST solution. Then, fluorescence was detected by using an EZ-Western detection kit (DOGEN, DAEILLAB SERVICE).

Figure 3:
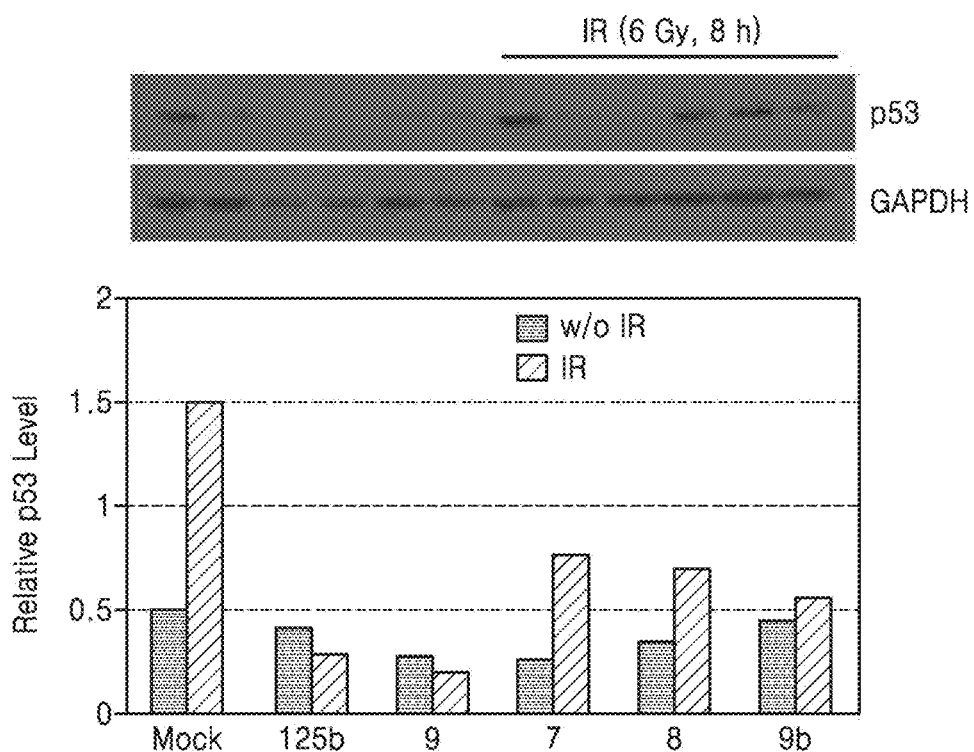
FIG. 3 shows the results of the expression of p53 protein in HCT116p53-LUC cells which were transfected with miRNAs and then irradiated, wherein the top part of FIG. 3 shows a result of western blot analysis, and the bottom part shows a graph illustrating the expression level of p53 protein level.

As shown in FIG. 3, the expression level of p53 in the groups transfected with one of the four selected miRNAs (hereinafter referred to as "treated group") was reduced to 50% or less compared to that of the Mock group (which was not transfected to miRNA), and it was confirmed that the reduction in the expression level of p53 in the treated groups was maintained even after the irradiation. The result showed that the selected miRNAs effectively reduce the expression of p53 protein.

2-2. Measurement of p53 mRNA Level Via Real-Time PCR

In order to confirm whether the reduction in p53 protein expression attributable to the selected miRNAs was due to the decrease in the level of p53 mRNA, a real-time polymerase chain reaction (RT-PCR) was performed as follows.

100 nM of respective miRNA was transfected into a human colon cancer cell line (HCT116 (p53 wild type)) in the same manner as in Example 2-1, and total RNA was extracted by using an RNeasy mini kit (QIAGen, U.S.A.), and a cDNA was synthesized by using a PrimeScript RT Master Mix (Takara, Japan) with 1 µg of RNA as a template. PCR was performed by using a qPCR SYBR Green 2× Master mix kit (m. Biotech, Korea), and the primer sequences used are shown below.

```
p53 forward primer:
                                   (SEQ. ID. NO: 2)
CTGCCTTCCGGGTCACTGCC, p53 reverse primer:
                                   (SEQ. ID. NO: 3)
TTGGGACGGCAAGGGGGACA, GAPDH forward primer:
                                   (SEQ. ID. NO: 4)
CCGTCTAGAAAAACCTGCC, GAPDH reverse primer:
                                   (SEQ. ID. NO: 5)
GCCAAATTCGTTGTCATACC.
```

Figure 4:
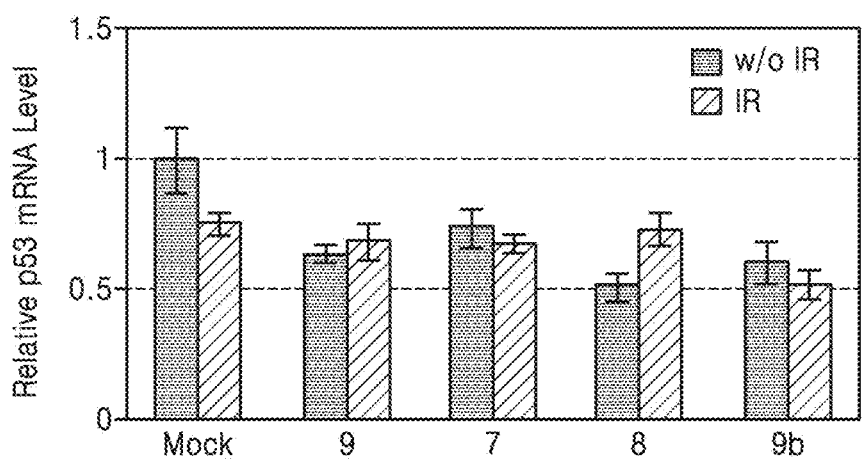
FIG. 4 is a graph illustrating the expression level of p53 mRNA in HCT116p53-LUC cells which were transfected with miRNAs and then irradiated.

FIG. 4 shows the p53 mRNA level in the Mock group and treated groups (9, 7, 8, and 9b) with and without irradiation. The overexpression of the 4 miRNAs selected in Example 1 did not lead to any significant change in the intracellular p53 miRNA levels. Accordingly, it was confirmed that the selected miRNAs reduces the expression of p53 via a translational regulation, rather than a transcriptional regulation.

2-3. Study of Radiation Sensitivity by Using HCT116p53 (Wild Type)

A clonogenic assay was performed in order to study the radiation sensitivity of cancer cells following the overexpression of the 4 miRNAs selected in Example 1. The miRNAs selected in Example 1 were respectively transfected into the human colon cancer cell line HCT116p53 in the same manner as in Example 2-1. 24 hours after the transfection, 100 cells and 2000 cells were plated on a 60 mm dish, respectively, and were irradiated on the following day with 0 Gy and 6 Gy, respectively. 10 days after the irradiation, colonies formed in each dish were dyed with 0.4% crystal violet, and the number of colonies was counted.

Figures 5, 6:
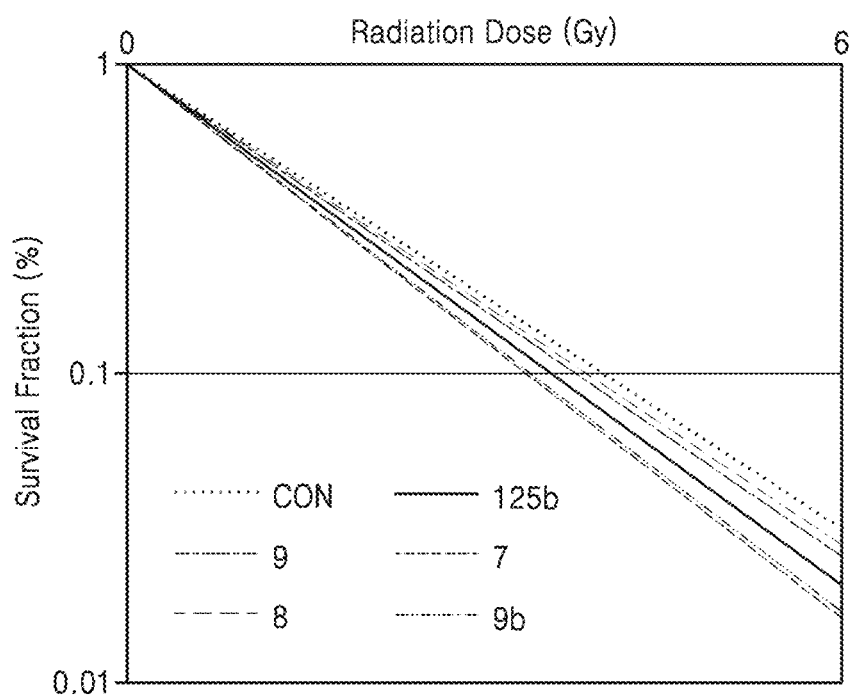
FIG. 5 is a graph illustrating the radiation sensitivity due to overexpression of miRNA after irradiation in HCT116p53 cells (wild type)
FIG. 6 shows the nucleotide sequence of miR-499b-5p (SEQ ID NO: 8) that binds to 3'-UTR of ATM (SEQ ID NO: 9 is wild-type ATM-3'UTR (middle sequence) and ATM-3'UTR 46 (bottom sequence) includes nucleotides 1-14 of wild-type ATM-3'UTR SEQ ID NO:9), a radiation specific target gene thereof, as confirmed by bioinformatic analysis (TargetScan)

FIG. 5 shows that the radiation sensitivity of the colon cancer cells significantly increased with the expression of miRNAs as compared to that of a control group wherein the cells were not transfected with any miRNA. Among the 4 miRNAs selected in Example 1, miRNA 9b showed the highest effect in enhancing the radiation sensitivity. The miRNA was confirmed to be miR-499b-5p.

Example 3

Characterization of Target Molecule of Selected miRNAs

An analysis was performed by using a program predicting an miRNA target regarding the 4 miRNAs selected in Examples 1 and 2 (see world wide web at targetscan.org).

As shown in FIG. 6, it was confirmed that the miR-499b-5p binds to a hexanucleotide sequence located in 3' UTR of ATM gene (positions 175 to 181 GUCUUAA (nucleotides 15-21 of SEQ ID NO:9): Human ATM NM_000051 3' UTR length: 3591) and thereby regulates the expression of ATM.

Example 4

Effect of miR-499b-5p Overexpression on Expressions of mRNA and Protein of ATM Gene In order to study the effect of the miR-499b-5p, which was selected based on a radiation sensitivity enhancing capability, on the expression of a target gene, the miR-499b-5p was transfected into a human breast cancer cell line MCF-7.

100 nM miR-499b-5p was transfected into the MCF-7 in the same manner as in Example 2-1, a western blot was performed, and then a real time PCR was performed by using the primers shown below in the same manner as in Example 2-2.

```
ATM forward primer:
                                   (SEQ. ID. NO: 6)
TGCTGACAATCATCACCAAGTTC, ATM reverse primer:
                                   (SEQ. ID. NO: 7)
TCTCCCTTCCTGTCCTGGAA.
```

Figure 7:
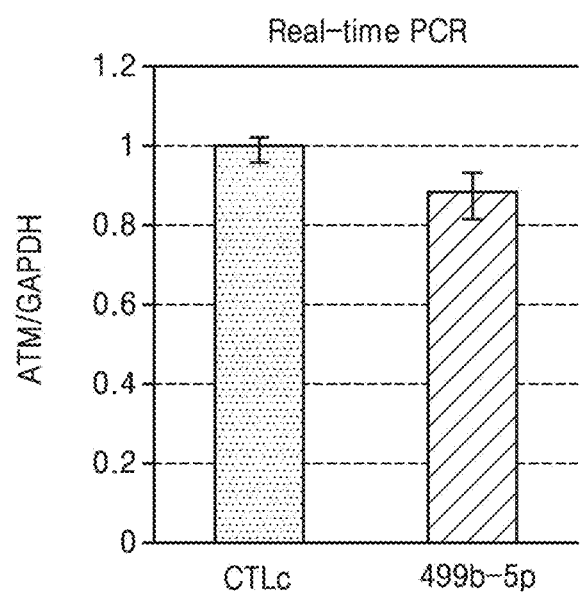
FIG. 7 shows a result of a real-time polymerase chain reaction (PCR) confirming the expression level of intracellular ATM mRNA due to overexpression of miR-499b-5p in MCF-7 cells, wherein the overexpression of miR-499b-5p did not produce any significant change in the expression of ATM mRNA.
Figure 8:
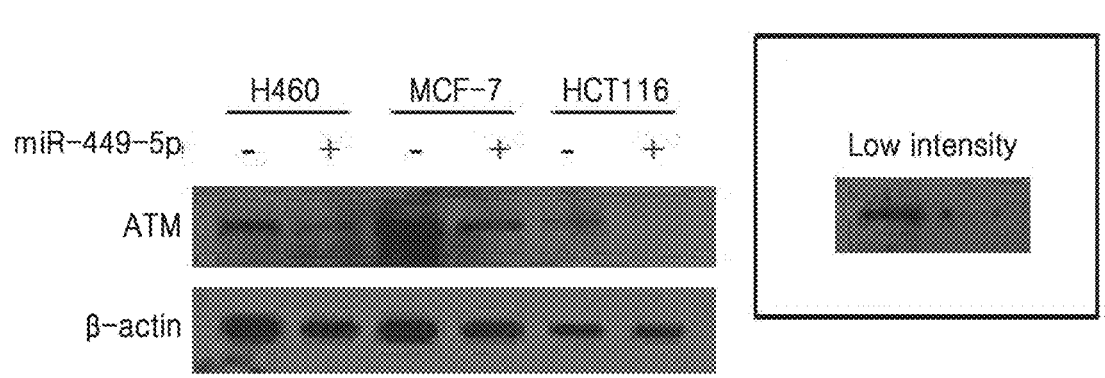
FIG. 8 shows the change in the level of ATM protein due to the overexpression of miR-499b-5p in MCF-7, H460, and HCT116 cells, wherein the image on the right side of FIG. 8 shows the level of ATM expression in MCF-7 cells observed with a shortened photosensitization time period (low intensity)
Figure 9:
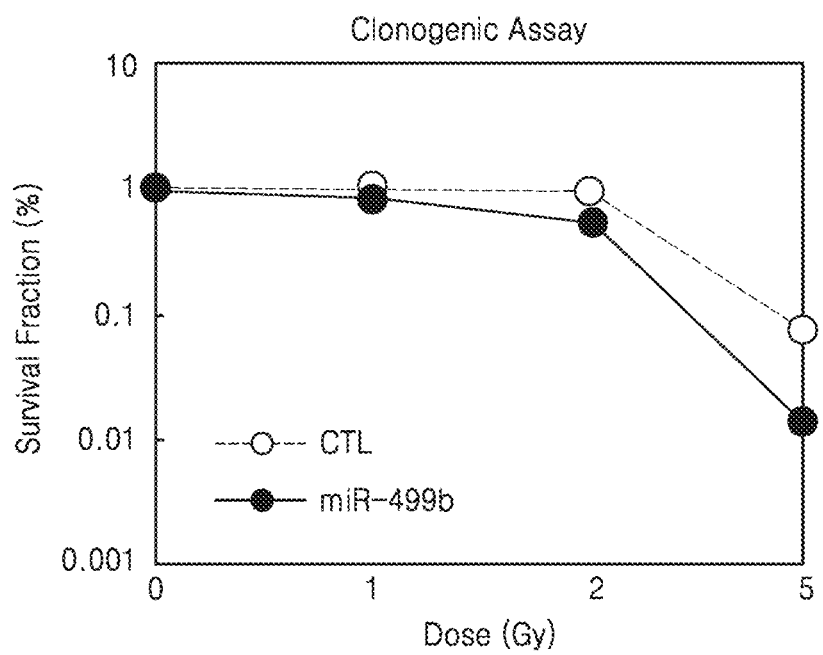
FIG. 9 is a graph illustrating an increase in radiation sensitivity due to the overexpression of miR-499b-5p in MCF-7 cells.

The result revealed, as shown in FIGS. 7 and 8, that the intracellular level of the ATM mRNA was not significantly affected by the overexpression of the miR-499b-5p, but the expression level of ATM protein was decreased.

In addition, various cancer cells were examined in the same manner as in Example 2-1 regarding the effect of miR-499b-5p overexpression on the expression of the ATM protein. As a result, it was confirmed that the level of ATM protein was reduced in the lung cancer cell line H460 and the colon cancer cell line HCT116, as well as in the breast cancer cell line MCF-7. The results are shown in FIG. 8.

Example 5

Effect of miR-499b-5p Overexpression on Radiation Sensitivity

In order to study the radiation sensitivity of breast cancer cells, the miR-499b-5p was transfected into the breast cancer cell line MCF-7 in the same manner as in Example 2-1. 24 hours after the transfection, 100, 200, 400, and 1000 breast cancer cells were added into a 60 mm dish, respectively, and were irradiated on the following day with 0, 1, 2 and 5 Gy, respectively. 10 days after the irradiation, colonies formed in each dish were dyed with 0.4% crystal violet, and the number of colonies in each dish was counted.

As a result, it was confirmed that the radiation sensitivity due to the overexpression of the miR-499b-5p, as compared to that of the control group (without any miRNA) started to show a difference from the radiation dose of 2 Gy and rapidly increased at the radiation dose of 5 Gy.

Example 6

Effect of miR-499b-5p Overexpression on Cell Proliferation

In order to study the change in proliferation of breast cancer cells due to the overexpression of miR-499b-5p, the miR-499b-5p was transfected into the breast cancer cell line MCF-7 in the same manner as in Example 2-1. 24 hours after the transfection, $1\times10^3$ breast cancer cells were added into each well of a 96-well plate. On the following day, irradiation (6 Gy) was applied and the level of cancer cell proliferation was measured at 2 day intervals starting from the date of irradiation by using EZ-Cytox kit (Daeil Lab Service, Korea).

Figure 10:
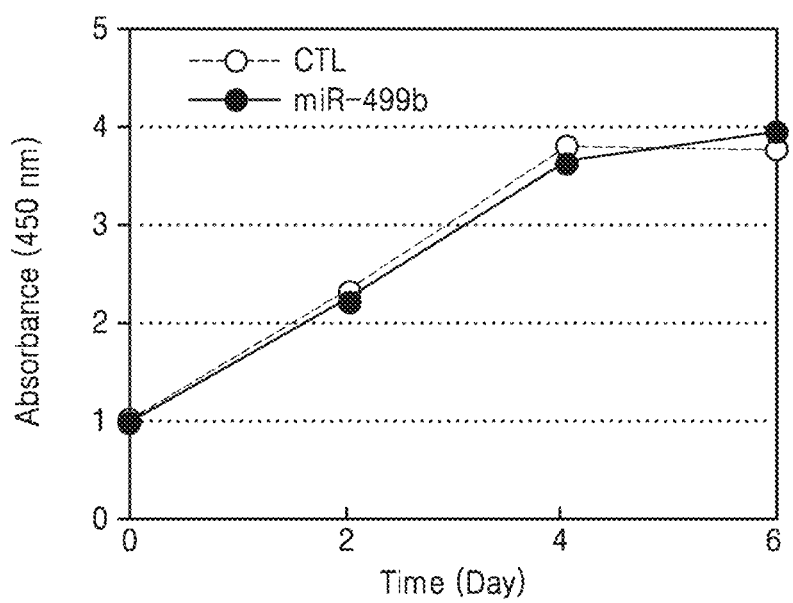
FIG. 10 is a graph illustrating an effect of the overexpression of miR-499b-5p on cell proliferation in MCF-7 cells.

The result revealed, as shown in FIG. 10, that the overexpression of miR-499b-5p does not have any significant effect on the breast cancer cell proliferation compared to that of the control group (which did not include any miRNA).

Accordingly, it was confirmed that the miR-499b-5p enhances the radiation sensitivity of breast cancer cells by reducing the protein expression level of ATM gene, which is involved in DNA repair mechanism.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

We claim:

1. A method of treating a radiation resistant cancer, the method comprising: administering miR-499b-5p of SEQ. ID. NO. 1 to a subject in need thereof, and applying radiotherapy, wherein the cancer is breast cancer, lung cancer, or colon cancer.

2. The method according to claim 1, wherein the miR-499b-5p binds to a 3'-UTR (untranslated region) of ATM (Ataxia telangiectasia mutated) gene, thereby reducing the expression of ATM gene.

3. The method according to claim 1, wherein the miR-499b-5p is present in an expression vector for intracellular delivery.

4. The method according to claim 1, wherein the miR-499b-5p enhances the radiation sensitivity of the cancer cells in the subject.

* * * * *